(12) United States Patent
Keller (10) Patent No.: US 7,736,049 B2
(45) Date of Patent: Jun. 15, 2010

(54) DEVICE AND METHOD FOR THE STORAGE MIXING AND DISPENSING COMPONENTS

(75) Inventor: Wilhelm A. Keller, Merlischachen (CH)

(73) Assignee: Medmix Systems AG, Rotkreuz (CH)

( * ) Notice: Subject to any disclaimer, the term of this patent is extended or adjusted under 35 U.S.C. 154(b) by 1120 days.

(21) Appl. No.: 10/568,543

(22) PCT Filed: Aug. 18, 2004

(86) PCT No.: PCT/CH2004/000517

§ 371 (c)(1),
(2), (4) Date: Feb. 17, 2006

(87) PCT Pub. No.: WO2005/018830

PCT Pub. Date: Mar. 3, 2005

(65) Prior Publication Data

US 2006/0227653 A1    Oct. 12, 2006

(30) Foreign Application Priority Data

Aug. 21, 2003  (CH) .................................... 1423/03

(51) Int. Cl.
*B01F 7/00* (2006.01)
*B01F 11/00* (2006.01)
*B01F 13/06* (2006.01)

(52) U.S. Cl. ............... 366/155.1; 366/139; 366/189; 366/195; 366/333

(58) Field of Classification Search ........... 366/189, 366/139, 176.1, 176.3, 154.1, 155.1, 167.1, 366/168.1, 195, 332, 333

See application file for complete search history.

(56) References Cited

U.S. PATENT DOCUMENTS

| 3,048,192 | A |   | 8/1962 | Murphy |
|---|---|---|---|---|
| 5,340,364 | A | * | 8/1994 | Ghelli et al. ............... 604/32 |
| 6,402,364 | B1 |   | 6/2002 | Aubert et al. |
| 6,550,957 | B2 | * | 4/2003 | Mizutani et al. ........... 366/189 |
| 7,073,936 | B1 | * | 7/2006 | Jonsson ..................... 366/139 |
| 7,080,936 | B1 | * | 7/2006 | Simpson ................. 366/162.3 |
| 7,175,336 | B2 | * | 2/2007 | Voellmicke et al. ...... 366/160.4 |
| 7,524,103 | B2 | * | 4/2009 | McGill et al. ............. 366/189 |
| 2003/0032964 | A1 | * | 2/2003 | Watkins et al. ............. 606/93 |

FOREIGN PATENT DOCUMENTS

| DE |      632579 |    | 9/1936 |
|---|---|---|---|
| DE | 202 14 747  | U1 | 1/2003 |
| EP |   0 292 472 |  A | 11/1988 |
| WO | WO 95/20408 | A1 | 8/1995 |
| WO | WO 00/35506 | A1 | 6/2000 |
| WO | WO 01/85070 | A1 | 11/2001 |

* cited by examiner

*Primary Examiner*—Tony G Soohoo
(74) *Attorney, Agent, or Firm*—Foley & Lardner LLP (57) ABSTRACT

The device for storing, mixing, and dispensing components is provided with means for mixing (6) a first component (27) with a second, liquid component (28) and for dispensing the mixed materials. The individual components (27, 28) are stored in respective containers (2, 3) that are arranged side by side, and a valve assembly (8) is arranged in the transfer area (7) between the outlet area (26) of the container (3) for storing the second, liquid component (28) and the liquid inlet (25) of the container (2) for storing the first component (27). Such a device allows an unproblematic storage of the different components without a local separation of the containers and an efficient mix thereof. This applies especially if the first component is a powder or a granular or porous substance, e.g. bone cement or bone replacement material.

16 Claims, 7 Drawing Sheets

FIG. 24 the text is too small to read reliably...

DEVICE AND METHOD FOR THE STORAGE MIXING AND DISPENSING COMPONENTS

BACKGROUND OF THE INVENTION

The present invention relates to a device and method for storing, mixing and dispensing components, comprising means for mixing a first component with a second, liquid component and for dispensing the mixture, according to the preambles of claims 1 and 15. The first component may be a powdery, granular, or porous bone replacement material or bone cement or a similar material for use in medicine or dentistry.

Devices according to the preamble of claim 1 are available on the market and generally comprise a container in which the powdery material is stored and to which the liquid component is added, the components being subsequently mixed and the mixture being dispensed by means of a piston.

The locally separated storage of at least two components may add complexity to stockkeeping and make the admixture of the smaller, liquid component problematic, e.g. due to confusion.

Further devices where the components are stored separately are known in the art, the smaller, liquid component being e.g. stored behind the piston or thrust rod of the chamber for the larger, powdery component. Arrangements of this kind generally comprise a valve that is arranged between the components and through which the liquid component may be supplied to the powdery component. The disadvantage of this solution is that no controllable transfer of the components is possible. U.S. Pat. No. 3,370,754 may be cited as an example standing for a number of references regarding this prior art.

A set for preparing and applying a tissue adhesive is known from EP-0 292 472, where in each case four syringe bodies are combined in pairs via a coupling member to form a respective unit. The coupling member comprises respective cones for receiving corresponding conical portions on the syringes. The reference only discloses a connection between two adjacent syringes, however without a valve arrangement, so that the possible applications are limited.

U.S. Pat. No. 6,402,364 discloses a dispenser for colored cosmetic compositions where a centrally arranged syringe is arranged to aspirate colors from one or another adjacent container via a screw lid having a channel in order to mix and dispense them. Such an arrangement is unsuitable for the medical field.

WO 00 35506 discloses a container for a powder and a container for a liquid for the preparation of bone cement where a coupling for vacuum is necessarily required, the connection between the two containers being basically always open and the container for the liquid being opened just before the mixing operation. However, selectively establishing a connection between the containers is not possible.

On the background of this prior art, it is the object of the present invention to provide a device and a method for storing, mixing, and dispensing components, more particularly powdery, granular, porous and liquid materials that allows a simple handling and arrangement of the containers while the components are fully separated during storage, and a simple control of the introduction of the second, liquid component into the first component, and that offers a wide range of applications such as external aspiration or introduction of a liquid into the dispensing device. The device attaining this object is defined in claims 1 and 15.

BRIEF DESCRIPTION OF THE DRAWINGS

The invention will be explained in more detail hereinafter with reference to drawings of exemplary embodiments.

FIG. 1 shows a first exemplary embodiment of a device of the invention, partly sectioned and in a perspective view, FIG. 2 schematically shows a detail of the solution according to FIG. 1, FIG. 3 shows a first exemplary embodiment of a valve in a section of FIG. 2, FIGS. 4-7 show different method steps during the transfer of one component into the other as well as during mixing and dispensing of the conditioned mixture in the device according to FIG. 1.

DETAILED DESCRIPTION OF THE INVENTION

Figures 1, 2, 3:
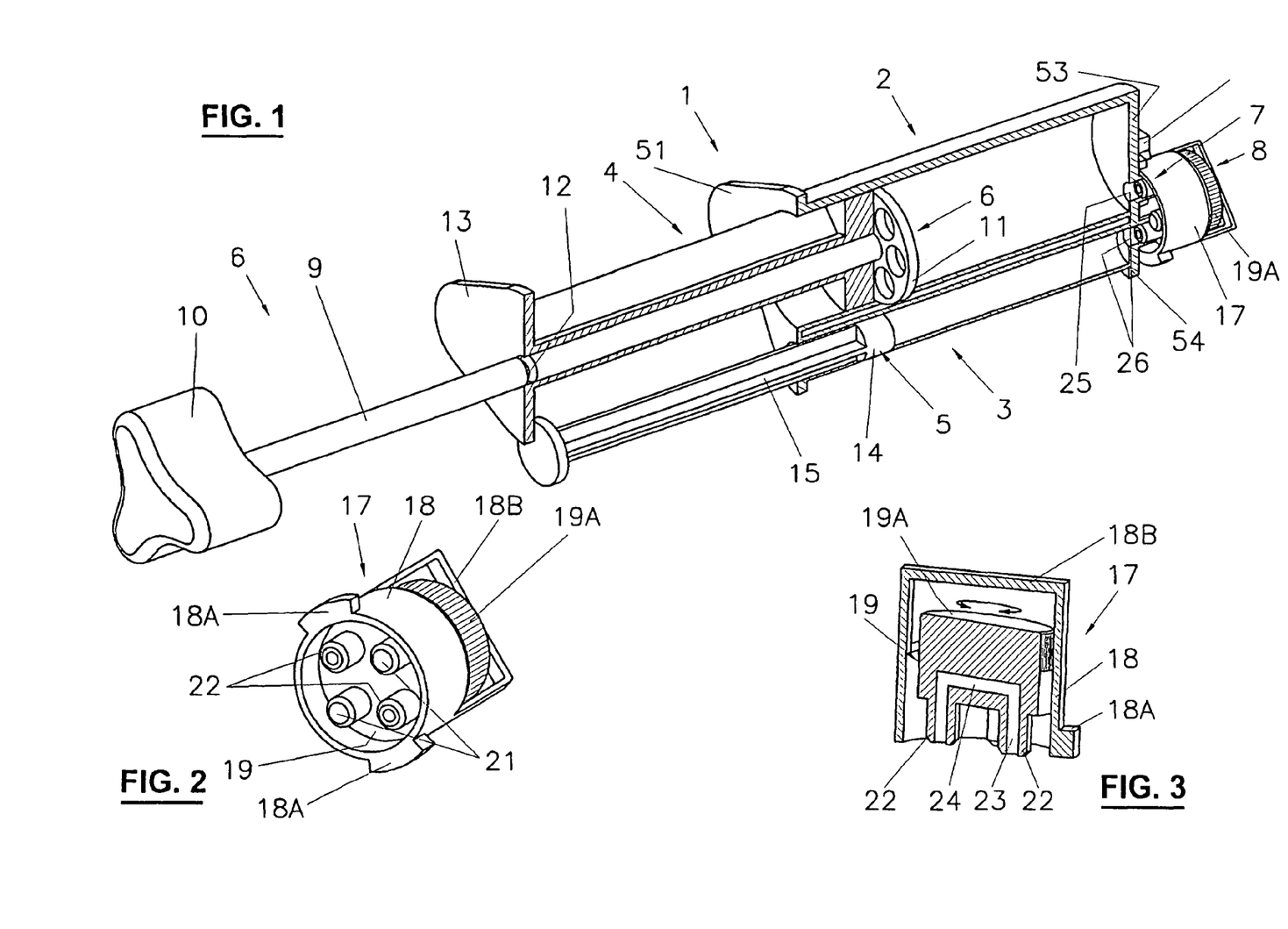

FIG. 1 schematically shows the basic structure of a device 1 of the invention in a first embodiment including a container 2 for a powdery material, a container 3 for a liquid material, a piston assembly 4 for dispensing the mixed materials, a piston assembly 5 for transferring the liquid component to container 2, and a mixing arrangement 6 for mixing the powdery and the liquid components in container 2, as well as a transfer area 7 between outlet area 26 of second container 3 and inlet 25 of first container 2. At the rear, the containers are provided with retaining flanges 51.

Alternatively, instead of a powdery material, the first component may be a liquid, granular, porous, or pasty material to which a liquid is admixed prior to dispensing. Hereinafter, however, reference is made to a powdery material by way of example, and for the sake of simplicity, the first container is designated as the powder container and the second or third container as the liquid container. Also, the dispensing devices may be commercial cartridges. Moreover, the term "mixing" here also includes the dissolution of one component in another.

Container 2 for the first component, a powdery material 27, and container 3 for the second, liquid component 28 are arranged side by side and separated by an air gap so that the risk of diffusion from one container to the other is substantially excluded. The side by side arrangement requires a connection between the liquid component and the powdery material, and means for selectively closing or opening the connection between the containers must be provided in transfer area 7. This is advantageously realized by a valve arrangement 8 as described below.

Mixing arrangement 6 is essentially composed of a mixing rod 9 that is movable back and forth in the container and provided with a turning knob 10 and a mixing member, in the present example a mixing disk 11, which is either perforated as in the present example and/or provided with peripheral cutouts or has another suitable design. Mixing disk 11 is capable of being both rotated and moved back and forth by means of the mixing rod and the turning knob in order to ensure a thorough mix of the powdery material and the liquid component.

The mixing arrangement is no longer used after the mixing operation, and therefore, as illustrated in FIG. 1, mixing rod 9 is provided with a predetermined breaking point 12 at the height of thrust plate 13 of the piston assembly approximately. At this point, the projecting end of the mixing rod including the turning knob can be broken off.

A mixing arrangement including a mixing rod that extends through the piston, a turning knob, and a mixing disk may also be used for other syringes or dispensing appliances without a valve arrangement.

Figure 8:
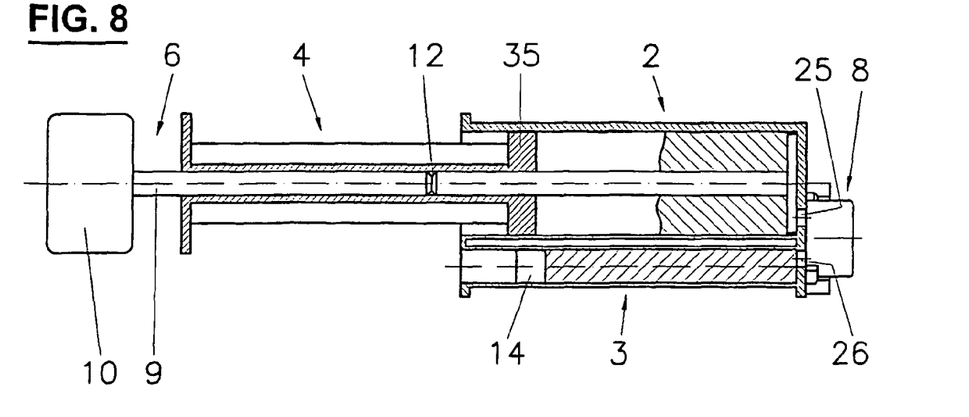
FIG. 8 shows an embodiment variant having a piston without a thrust rod for the second, liquid component.

With regard to the piston assembly for the second, liquid component, two variants are generally possible, i.e. a piston assembly having a piston 14 and thrust rod 15 or a piston assembly according to FIG. 8 having only a piston 14 that is displaceable by negative pressure.

FIGS. 1-3 illustrate a first embodiment of valve arrangement 8 that is in the form of a valve cap 17 having an enclosure 18 with a bracket 18B and two bayonet lugs 18A engaging in corresponding sockets 16 and 20 arranged on enclosure bottom 53 of container 2 and enclosure bottom 54 of container 3. Inside cap enclosure 18, a plug assembly 19 of two pairs of plugs 21 and 22 is arranged that is reversible with respect to the enclosure and comprises a knob 19A that projects from the enclosure. Plugs 21 are solid and serve as closures of transfer area 7, whereas plugs 22 are provided with respective bores 23 that are interconnected by a connecting channel 24, as appears in FIG. 3.

Depending on which pair of plugs is inserted in inlet 25 of container 2 and outlet 26 of container 3, the two containers are either connected to each other or not. By removing the cap, rotating the plugs by 90° and reconnecting it by means of the bayonet lock, the connection is selectively interrupted or established.

Figure 4:
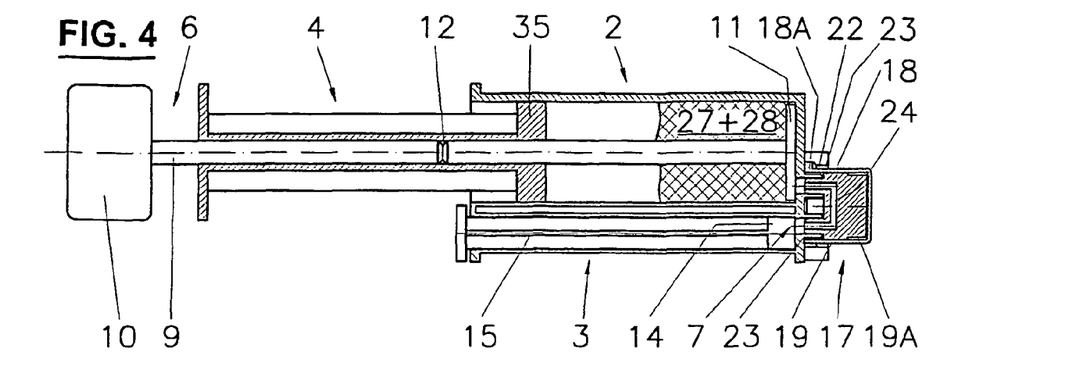
Figure 5:
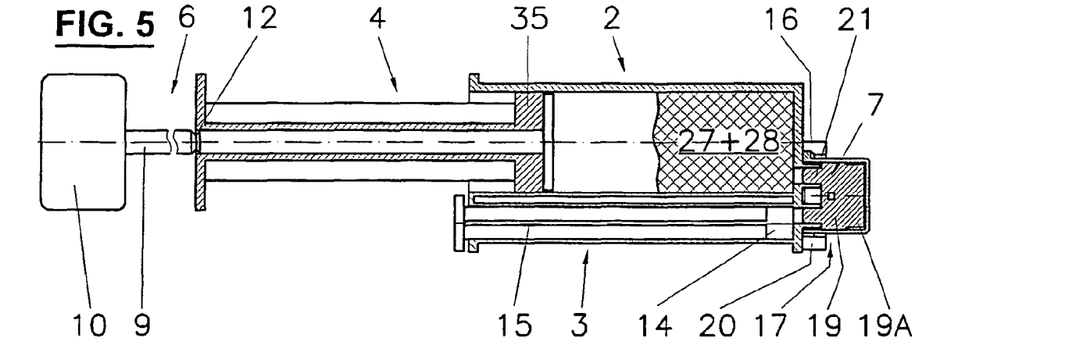

FIGS. 4-7 illustrate four different phases in the application of a device according to FIG. 1. In the illustration of FIG. 4, piston assembly 5 has been operated to inject liquid 28 into container 2, and according to FIG. 5, after changing the valve from open to closed, it has been mixed with powder 27 by means of mixing arrangement 6.

Figure 6:
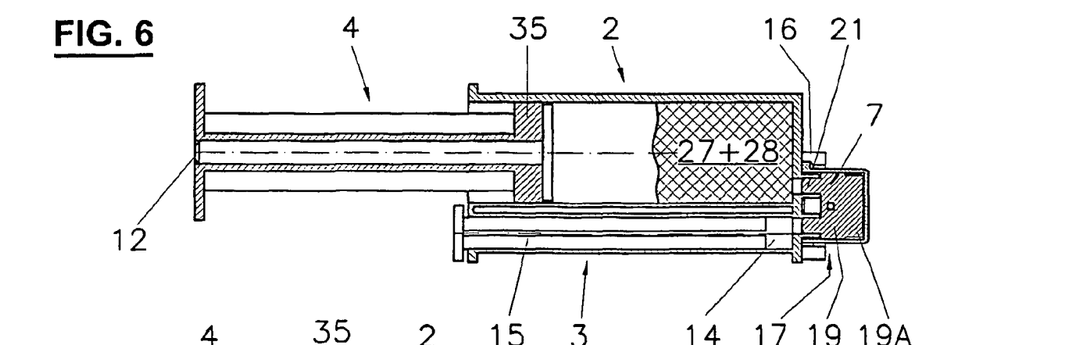
Figure 7:
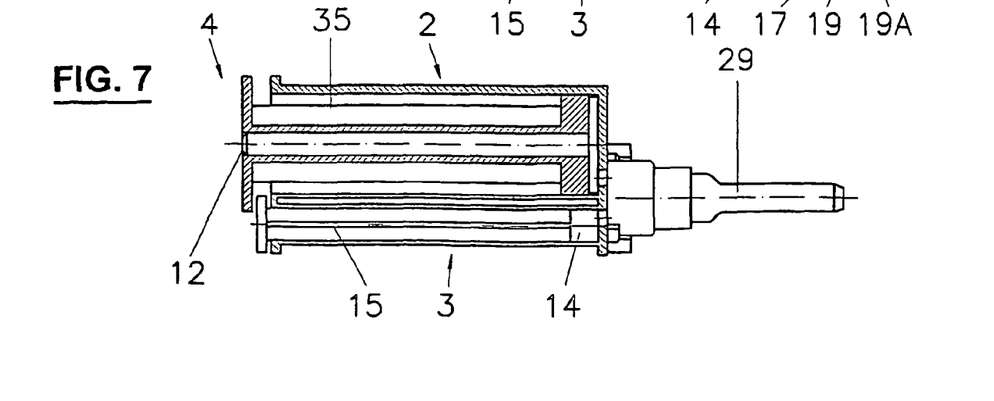

In the illustration of FIG. 6, the mixer rod end of the mixing arrangement has been broken off at the predetermined breaking point and then removed so that the device is ready for dispensing after removing the valve cap. In the illustration of FIG. 7, a dispensing tip 29 has been attached and the mixture dispensed by piston assembly 4.

In the embodiment variant according to FIG. 8, piston 14 in container 3 is actuated by negative pressure rather than by a thrust rod. By retracting piston assembly 4 with piston 35 from an intermediate position, a negative pressure is generated by which piston 14 in container 3 is moved in the direction of outlet 26. To this end, there must be an open connection between outlet 26 and inlet 25. In this variant it is useful if the wall of container 2 comprises an internal groove or bead and piston 35 comprises corresponding means for preventing it from being pulled out completely.

Figure 9:
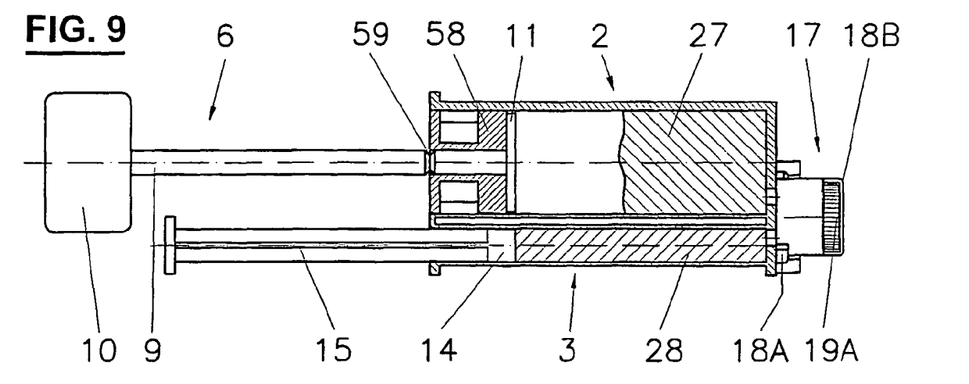
FIG. 9 shows a second exemplary embodiment of the dispensing piston without a thrust rod.

In another embodiment variant according to FIG. 9, piston 58 of the cartridge or of container 2 is not actuated by a thrust rod that is connected thereto but by the thrust rod of a dispensing appliance, and predetermined breaking point 59 of mixing rod 9 is nearer to the piston. Piston 58 should have a sufficient axial length to prevent canting of piston 58 when the mixing rod is broken off at predetermined breaking point 59.

Figure 10:
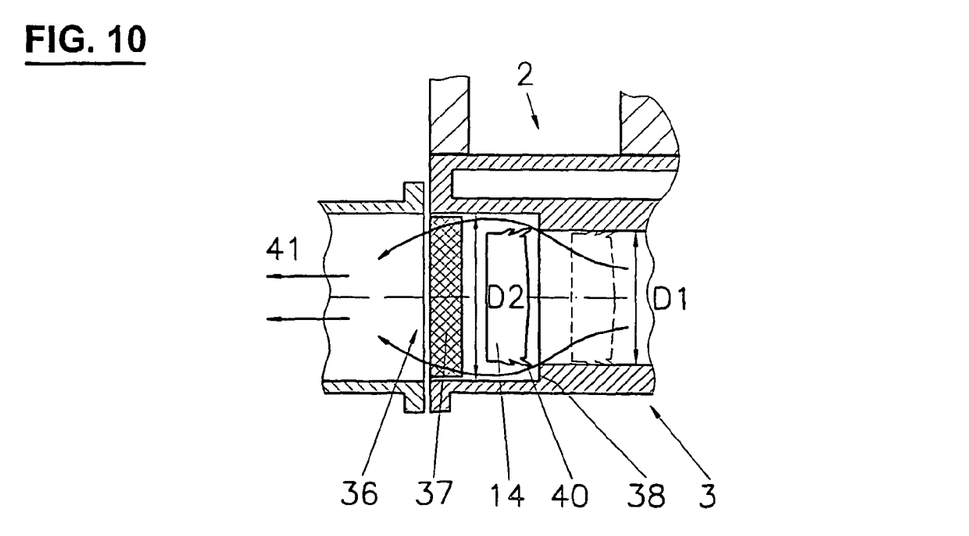
FIG. 10 shows another exemplary embodiment having a vacuum coupling.

In an application of the arrangement under vacuum according to FIG. 10, a vacuum source is connected to empty liquid container 3 that communicates with powder container 2 and applies vacuum to the latter in order to mix under vacuum. FIG. 10 illustrates the inlet end 36 of container 3 in whose closure a filter 37 is incorporated. Internal diameter D2 of the inlet end is larger than that D1 of the rest of the container, thereby forming a shoulder 38. FIG. 10 illustrates the aspiration after piston 14, here provided with sealing lips 40, has been actuated to transfer the liquid into container 2. By the application of vacuum, symbolically indicated by arrows 41, piston 14 is retracted until the sealing lips reach enlarged area D2, thereby allowing the air contained in the containers to escape, which is a prerequisite for an optimally air-free, thorough mix of certain powders such as PMMA. Filter 37 may also be located in the vacuum coupling nozzle.

Figure 11:
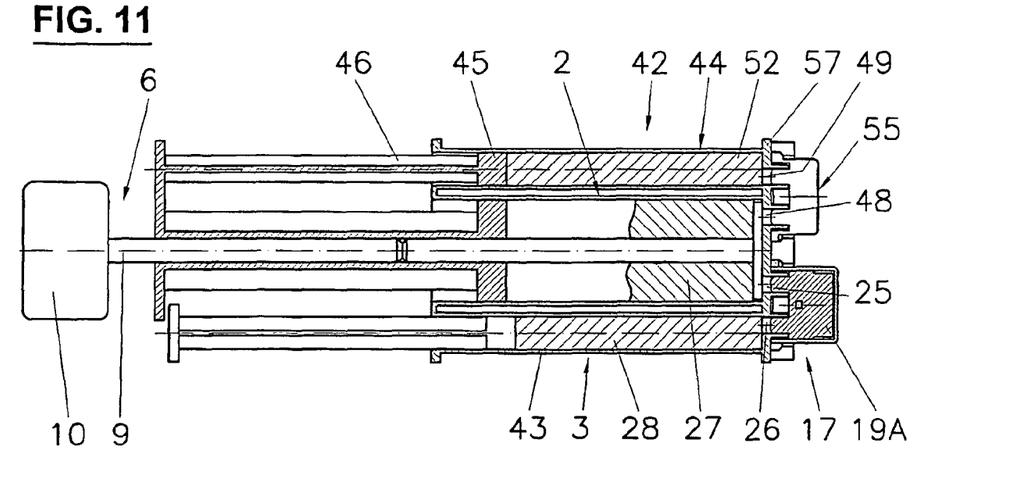
FIG. 11 shows another exemplary embodiment of a device according to the invention.
Figure 12:
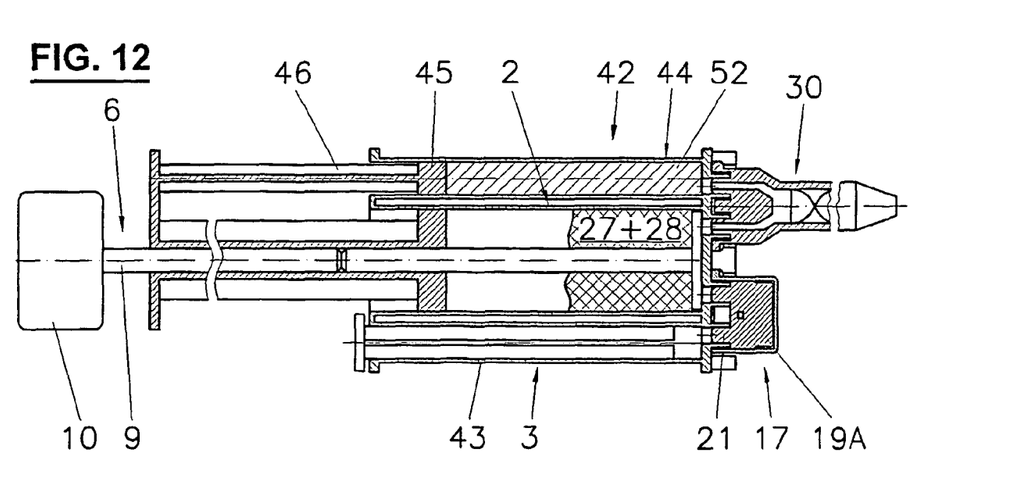
FIG. 12 shows the device of FIG. 11 in a different outlet configuration and position of a thrust rod.

FIGS. 11 and 12 illustrate a device 42 where a third container 44 is arranged in enclosure 43 next to the two containers 2 and 3. This third container 44 including piston 45 and thrust rod 46 may be designed like container 3 with a piston and thrust rod but may possibly have a different dimension, and it is filled with another liquid component 52, e.g. with a hormone, with antibiotics or the like.

In the starting position of FIG. 11, outlet 48 for the mixture from containers 2 and 3 and outlet 49 of container 44 are sealed by a common closure 55 that interrupts the connection as long as the first liquid transferred to the powder is being admixed. For dispensing the second liquid and the mixture, the closure is removed and a mixer 30 or an accessory is attached to common outlet 47. To this end, the usual bayonet coupling members in enclosure bottom 57 may be used.

FIG. 12 suggests that the liquid from container 3 has first been transferred to container 2 and subsequently the mixture from container 2 and the component from container 44 are dispensed through the common mixer.

Based on FIGS. 11 and 12, not only one but also further additional containers similar to container 44 can be arranged around container 2, each comprising a respective closure of the outlets and a common coupling of the container outlet and of the outlet of container 2.

Figure 13:
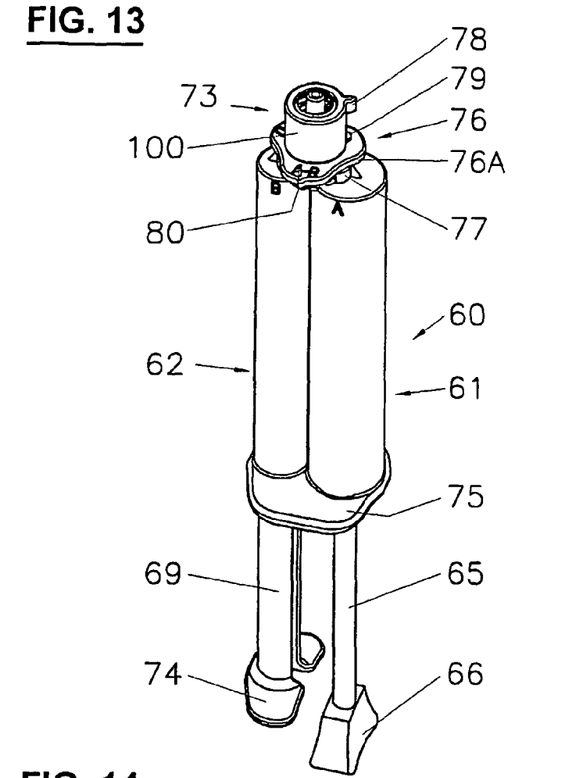
FIG. 13 shows a perspective view of another exemplary embodiment of a device according to the invention for aspirating a liquid, mixing the latter with a powder, and dispensing the mixture.

In FIGS. 13 to 18, an appliance according to the invention is indicated that allows aspirating a liquid, e.g. blood, mixing it with a powder, and dispensing the mixture. FIG. 13 shows a perspective view of appliance 60 including powder container 61, marked "A", for powder 71 and a liquid container 62, marked "B", for a liquid 72. On the inlet side, mixing rod 65 with turning knob 66 and loose thrust rod 69 with thrust flange 74 as well as retaining flange 75 are visible.

Figures 16, 17, 18, 19:
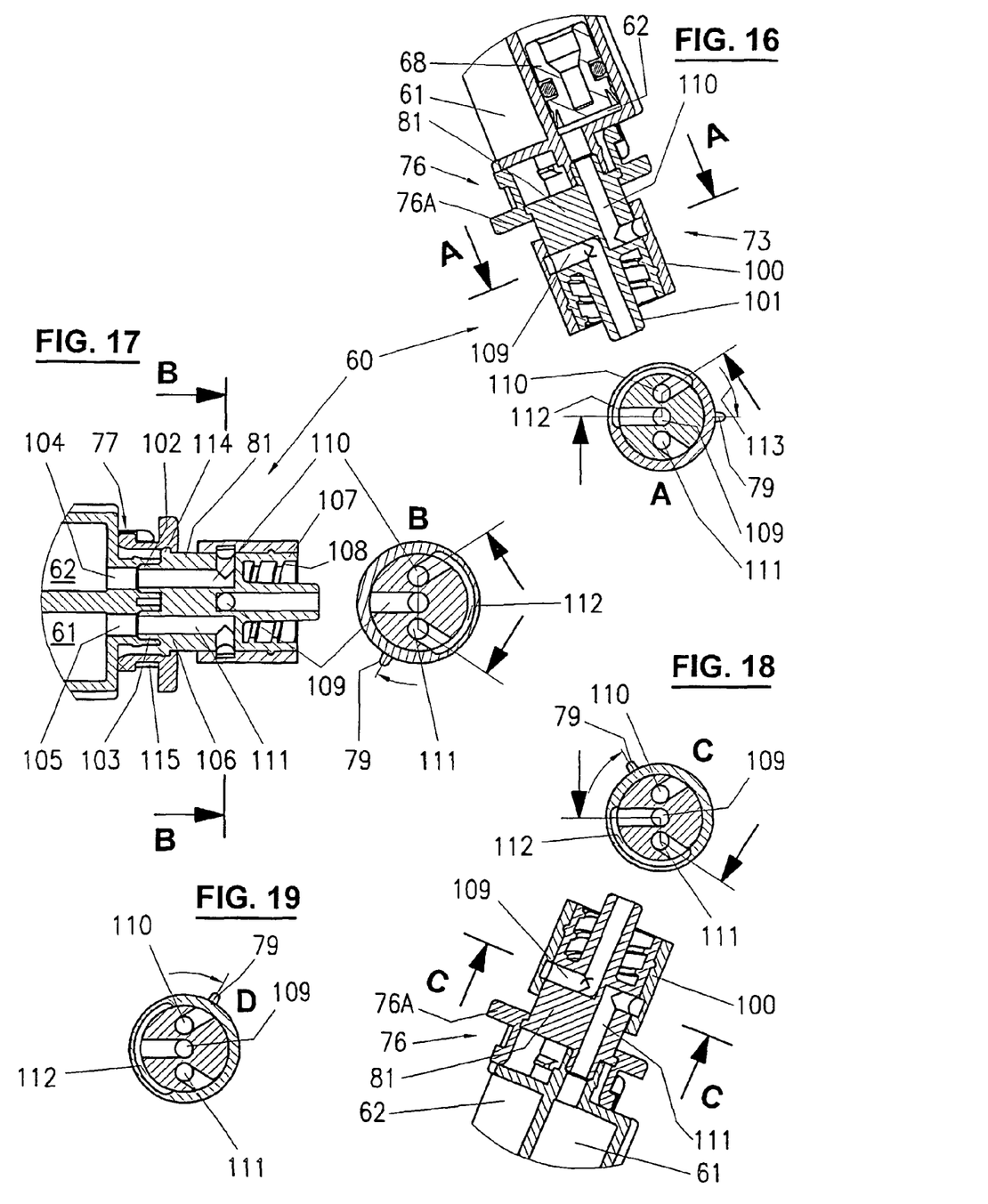
FIG. 16 shows an enlarged detail of the inlet/outlet area in the form of a three-way valve of the syringe of FIG. 13 and a section A according to line A-A.
FIG. 17 shows the inlet/outlet of FIG. 16 in a different section plane and a section B according to line B-B.
FIG. 18 shows the inlet/outlet of FIG. 16 in a further section plane and a section C according to line C-C.
FIG. 19 shows the closed position of the valve in a fourth section D.

Located on the outlet side is valve assembly 73 including fastening portion 76 with bayonet coupling members 77 and rotary ring 100 whose free end is provided with a handle portion 78 and near indicator disk 76A of fastening portion 76 with a pointer 79, pointer 79 indicating the current position of the three-way valve on indicator disk 76A, for example A—B, connection between the two storage containers or A—O or B—O, connection between container A or container B and the inlet/outlet, or according to FIG. 19 the closed position. For alignment during the attachment of the valve assembly, the fastening portion is provided with a nose 80.

The valve assembly may be fastened in another manner than by bayonet coupling members, e.g. by means of a rotationally secure snap-on connection that may also be provided directly on the valve body.

Near the inlet, a piston 63 is arranged in powder container 61 through which mixing arrangement 64 with mixing rod 65, turning knob 66 and mixing disk 67 passes. Liquid container 62 is provided near its inlet with a piston 68 that is displaceable toward outlet 70 by means of a separate, loose thrust rod 69.

Figure 14:
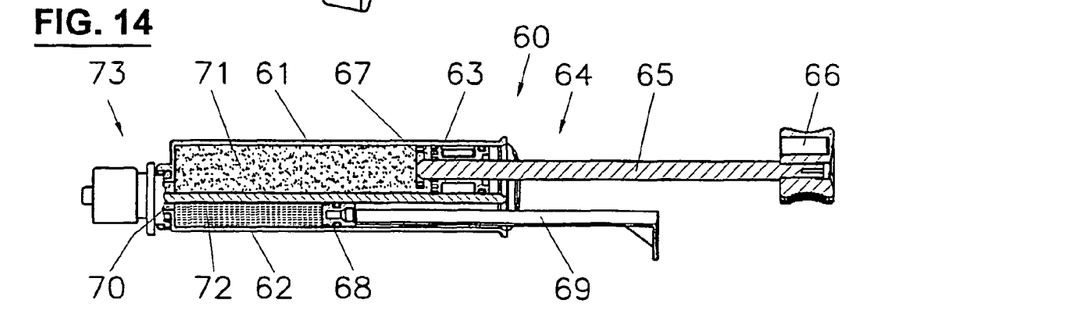
FIG. 14 shows the device of FIG. 13 in a partial longitudinal section just before use.
Figure 15:
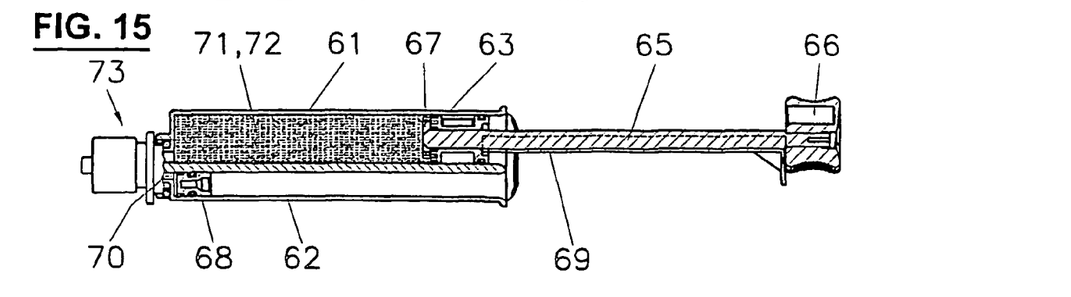
FIG. 15 shows the device of FIG. 14 after the transfer of the liquid.

In the application of double syringe 60 as in the preceding examples, i.e. for transferring the liquid, mixing, and dispensing, between the illustrations of FIG. 14 and FIG. 15, thrust rod 69 has been thrust in completely, liquid 72 has been transferred from liquid container 62 to powder container 61, thrust rod 69 has been drawn off and then pushed in between piston 63 and the underside of turning knob 66 such that when pressing on the mixing rod, the latter actuates piston 63 via thrust rod 69 to dispense mixture 71+72. To this end, the cross-section of the thrust rod may be a little more than semi-circular in shape so as to partially enclose the mixing rod and clamp it by its profile.

In the illustrations of FIGS. 14 and 15, valve assembly 73 has only been represented and described summarily in order to explain the operation of the loose thrust rod. The detailed description of valve assembly 73 follows with reference to FIGS. 16-19.

Dispensing appliance 60 according to FIGS. 16 to 19 is primarily useful also for receiving a liquid such as e.g. blood in liquid container 62 and subsequently mixing it with the powder after its transfer to the powder container, and then dispensing it. To this end, the containers are connected to each other or to common inlet/outlet 101 via rotary ring 100.

Also, the thrust rod and the piston end are so designed that the thrust rod can be coupled for retracting the piston by the thrust rod in order to aspirate a liquid. This coupling may e.g. be realized by providing an offset circular step having a slightly smaller diameter than the piston on the thrust rod side of the piston end, an internal groove at the piston side end of the slightly more than semicircular thrust rod being slidable thereon or releasable therefrom.

Valve assembly 73 in the form of a three-way valve is essentially composed of fastening portion 76, a valve body 81 that is secured thereto, and a rotary ring 100. Valve body 81 includes a coupling portion 106 that is insertable in the two container outlets 104 and 105 by coupling nozzles 102 and 103 and is followed on its outlet side by inlet/outlet portion 107. Coupling portion 106 is maintained in a circular groove 115 of fastening portion 76 by means of a circular collar 114.

Inlet/outlet portion 107 is provided with a bore 109 that is angled and ends at the periphery of the inlet/outlet portion. Analogously, inlets/outlets 110, 111 of coupling portion 106 of the valve body also end at the periphery, as appears most clearly in FIG. 17, and more specifically at the same height as the orifice of bore 109 in the inlet/outlet. Inlet/outlet portion 107 is surrounded by rotary ring 100, which is retained on coupling portion 106 and extends beyond the peripheral entrances/exits of the inlets/outlets and is provided with an internal groove 112 that extends over a little more than a third of the circumference, as appears in sectional views A, B, C, D.

As appears when comparing FIGS. 16 to 19 or A, B, C, and D, respectively, internal groove 112, depending on the position of the rotary ring, either connects liquid container 62 to common inlet/outlet 101, FIG. 16, A, the two inlets/outlets 110 and 111 to each other, FIG. 17, B, or powder container 61 to common inlet/outlet 101, FIG. 18, C, or the rotary ring is in a closed position, D, FIG. 19, without a connection to any inlet or outlet.

In the position of FIG. 16, a liquid, e.g. blood can be aspirated by retracting piston 68. In the position of FIG. 17, the rotary ring has been rotated by 120°, thereby connecting the two containers to each other and allowing the liquid to be transferred to the powder container. After a further rotation of the rotary ring by 60°, both containers are closed and the mixture can be mixed. Then the valve assembly is brought to the position of FIG. 18, thereby allowing the mixture in powder container 61 to be dispensed. It is also possible to aspirate another liquid into the liquid container, to transfer it to the powder container and to mix it subsequently.

Figure 20:
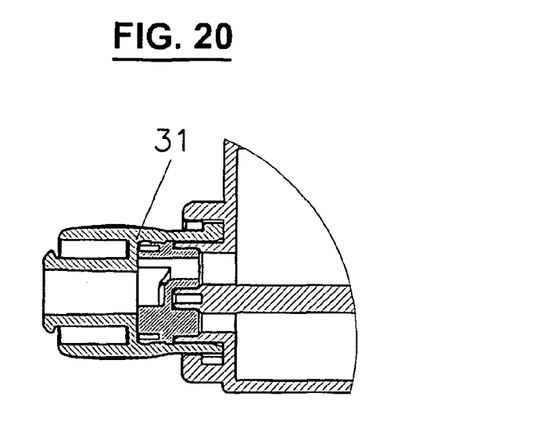
FIG. 20 shows a further outlet accessory.

Inlet/outlet 101 is in the form of a Luer connector having a thread 108 and allowing the connection either of another syringe or of an outlet attachment. However, it is also possible to disconnect the valve assembly by means of the bayonet coupling and to attach another connecting part, e.g. another Luer connector 31 of common use, see FIG. 20, by means of the bayonet connection.

Valve assembly 73 may alternatively be used for other devices than the described ones, e.g. in a general manner as a three-way valve with a rotary ring having a partial circular internal groove for connecting two container inlets/outlets either to each other or each to a common inlet/outlet, or closing all inlets/outlets. Again, in such an embodiment, the valve assembly may be fastened in another manner than by bayonet coupling members, e.g. by means of a rotationally secure snap-on connection that may also be provided directly on the valve body, i.e. without a fastening portion.

Other valve assemblies are also possible, e.g. an automatic valve assembly or a simple rotary or flat sealing rotary valve having a turning knob with a groove, which either establish or close a connection.

FIGS. 21-24 illustrate that instead of being made of one piece, the multicomponent syringes or cartridges may be manufactured and filled as separate storage containers that are joined prior to use and when required.

Figure 21:
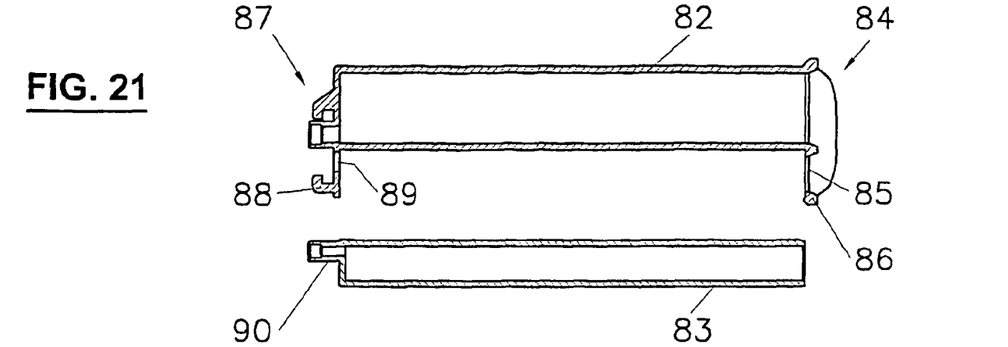
FIG. 21 shows a two-component syringe having separate storage containers.
Figure 22:
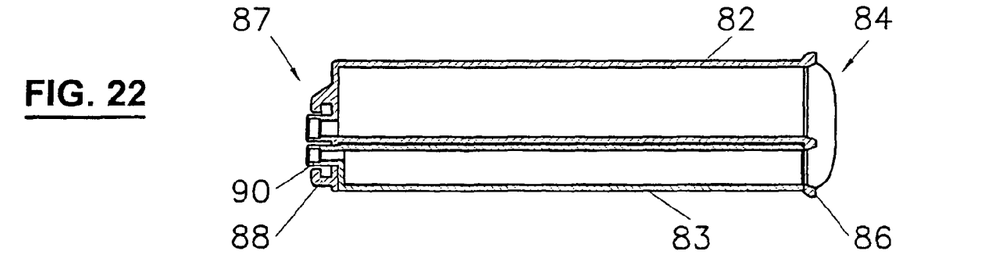
FIG. 22 shows the assembled two-component syringe of FIG. 21.

FIGS. 21 and 22 illustrate a powder container 82 and a liquid container 83, the container of the larger cross-section, i.e. powder container 82, comprising a retaining flange 84 whose part 85 that extends beyond container 82 serves for receiving the second container 83. For this purpose, the projecting part 85 is provided with a circular bead 86 on its circumference.

On the outlet side, the larger container has an outlet flange 87 comprising the usual bayonet coupling means 88 as well as an opening 89 for receiving the outlet 90 of the smaller container. The described arrangement also applies to 1:1 containers.

Figure 23:
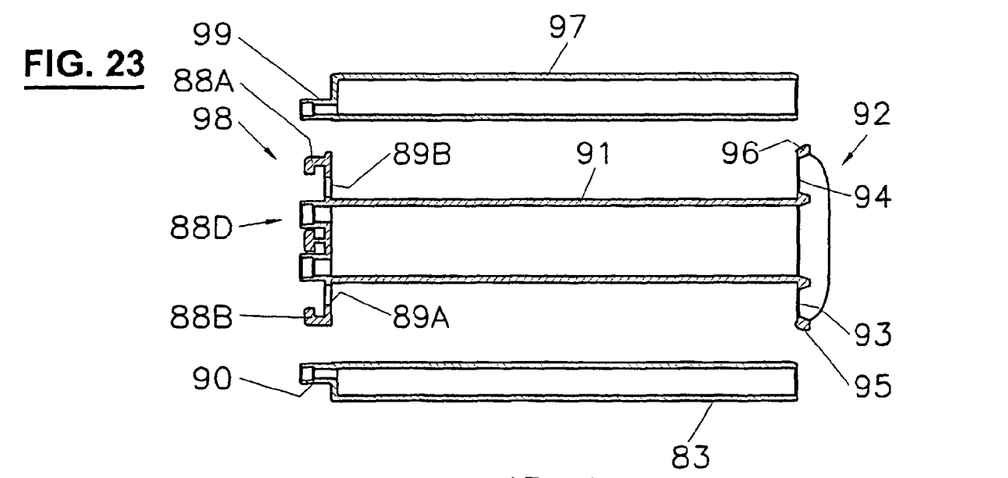
FIG. 23 shows a three-component syringe having separate storage containers.
Figure 24:
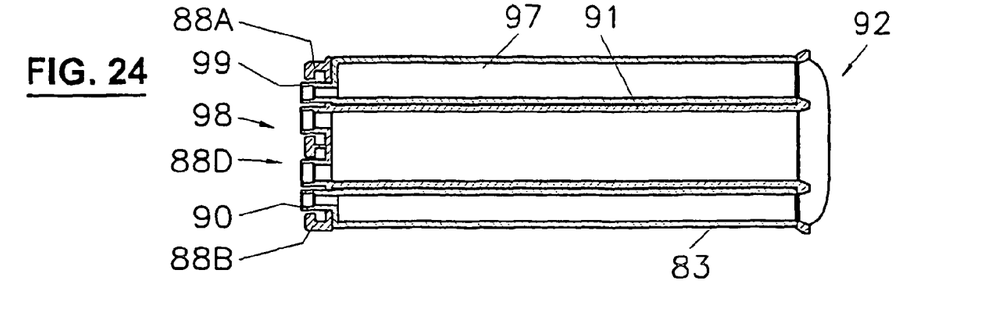
FIG. 24 shows the assembled three-component syringe of FIG. 23.

Correspondingly, the same applies for a three-component syringe arrangement according to FIGS. 23 and 24. Powder container 91 comprises a retaining flange 92 having two projecting parts 93 and 94 that are each provided with circular beads 95 and 96 extending around parts 93 and 94 that serve for retaining liquid containers 83 and 97, respectively. Outlet flange 98 comprises two bayonet coupling lugs 88A and 88B and a central double bayonet lug 88D as well as two openings 89A and 89B for receiving outlets 90 and 99 of the respective liquid containers. The two bayonet couplings serve for connecting containers 91 and 83 or 91 and 97 that may either be provided with a valve assembly or an outlet attachment or a mixer.

In the illustrated exemplary embodiments, the outlet of the liquid container is inserted in opening 89A or 89B and the container is snapped in over bead 86 or 95, 96. The connection and attachment of the individual containers forming a two-, three-, or multicomponent dispensing appliance may alternatively be achieved by other means, e.g. by means of snap-on connections or the like. Also, a double syringe or double cartridge may be connected to a further separate container in this manner.

The invention claimed is:

1. A device for storing, mixing, and dispensing components, comprising:
   a mixing arrangement configured to mix a first component with a second, liquid component; and
   a dispensing arrangement configured to dispense the mixed material,
   wherein the individual components are disposed in respective containers that are arranged side by side,
   wherein a closure or a connecting channel is selectively provided in a transfer area between the outlet area of the container configured to store the second, liquid component and the liquid inlet of the container configured to store the first component,
   wherein the mixing arrangement is arranged in the container configured to store the first component that is separated from the dispensing arrangement,
   wherein the mixing arrangement includes a mixing rod with a mixing member that is movable back and forth and rotatable in the container configured to store the first component, and
   wherein the mixing rod includes a predetermined breaking point.

2. The device according to claim 1, wherein the mixing member is a mixing disk that is perforated and/or provided with peripheral cutouts.

3. The device according to claim 1, wherein a valve assembly is arranged in the transfer area in order to selectively provide the closure or the connecting channel.

4. The device according to claim 3, wherein the valve assembly is a valve cap that is removably attachable to an enclosure bottom of the containers for the first and the second, liquid components and includes two pairs of plugs of which one pair are solid plugs and the other pair are plugs that are connected to each other by the connecting channel, the valve cap being attachable such that the plugs either leave open or interrupt the connection in the transfer area.

5. The device according to claim 4, wherein the valve cap further includes a plug arrangement of the solid and the interconnected plug pairs that is arranged reversibly with respect to a cap enclosure.

6. The device according to claim 3, wherein the valve assembly includes a three-way valve having a rotary ring with a circular internal groove that extends over a part of the circumference that is configured to connect either the first component with a first common inlet/outlet portion, a second component with a second common inlet/outlet portion, or a first inlet/outlet of the container to a second inlet/outlet of the container or is configured to close all the inlets/outlets.

7. The device according to claim 6, wherein the three-way valve includes a valve body having a fastening portion arranged on its container side and the rotary ring secured to its outlet side.

8. The device according to claim 3, wherein a common inlet/outlet portion of the valve assembly is provided with a coupling accessory or element that allows the connection of a syringe.

9. The device according to claim 1, wherein the first component is a powdery, granular, or porous material.

10. The device according to claim 1 for mixing under vacuum, wherein at its inlet end, the container for the second, liquid component includes a section having a greater diameter than the diameter of the rest of the container.

11. The device according to claim 1, wherein the piston for the second, liquid component is either actuated by a thrust rod or movable by negative pressure.

12. The device according to claim 1, wherein the mixing rod is configured to push a thrust rod in between the underside of the turning knob of the mixing rod and a piston of a powder container such that the mixture is dispensed.

13. The device according to claim 12, wherein the piston side end of the loose thrust rod and the thrust rod side end of the piston are so designed that the thrust rod can be coupled to the piston in order to apply traction to the latter, and uncoupled therefrom in order to remove it after use.

14. The device according to claim 1, wherein the containers are in the form of separate parts that can be assembled.

15. The device according to claim 14, wherein the first container includes a retaining flange with one or two part(s) extending beyond the container and provided with circular bead(s) configured to receive the second container or the second container and a third container, the outlets of the the second container and the third container configured to push through openings in the outlet flange of the first container.

16. The device according to claim 1, wherein the outlet flange of the containers is provided with a coded bayonet coupling device.

* * * * *